United States Patent
Lin et al.

(10) Patent No.: US 7,509,183 B2
(45) Date of Patent: Mar. 24, 2009

(54) INTEGRATED GLOBAL LAYOUT AND LOCAL MICROSTRUCTURE TOPOLOGY OPTIMIZATION APPROACH FOR SPINAL CAGE DESIGN AND FABRICATION

(75) Inventors: Chia Ying Lin, Ann Arbor, MI (US); Scott J. Hollister, Ann Arbor, MI (US); Cheng-Yu Lin, Fremont, CA (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 10/553,851

(22) PCT Filed: Apr. 22, 2004

(86) PCT No.: PCT/US2004/012375

§ 371 (c)(1),
(2), (4) Date: Aug. 7, 2006

(87) PCT Pub. No.: WO2004/093657

PCT Pub. Date: Nov. 4, 2004

(65) Prior Publication Data

US 2006/0276925 A1    Dec. 7, 2006

Related U.S. Application Data

(60) Provisional application No. 60/464,703, filed on Apr. 23, 2003.

(51) Int. Cl.
*G06F 19/00* (2006.01)
(52) U.S. Cl. .................................. 700/97; 700/118
(58) Field of Classification Search ........... 700/97–110, 700/118; 623/17.16, 17.15
See application file for complete search history.

(56) References Cited

U.S. PATENT DOCUMENTS

| | | | |
|---|---|---|---|
| 6,425,920 B1 | 7/2002 | Hamada | |
| 6,443,989 B1 | 9/2002 | Jackson | |
| 6,471,724 B2 | 10/2002 | Zbedlick et al. | |
| 2002/0169507 A1* | 11/2002 | Malone | 623/17.11 |
| 2002/0173850 A1* | 11/2002 | Brodke et al. | 623/17.11 |
| 2003/0009235 A1* | 1/2003 | Manrique et al. | 623/23.63 |
| 2004/0213443 A1* | 10/2004 | Haussecker et al. | 382/128 |

\* cited by examiner

*Primary Examiner*—Kidest Bahta
(74) *Attorney, Agent, or Firm*—Harness, Dickey & Pierce, P.L.C.

(57) ABSTRACT

A method of designing an interbody fusion cage is disclosed. The method uses topology optimization algorithms to define the structural layout and the inner microstructures of the cage. After the structural layout is defined, a density distribution process is performed. Based on the density distribution, the inner microstructures of the cage are defined.

20 Claims, 9 Drawing Sheets

Max = 1.00e+00
Min = 6.06e-02

INTEGRATED GLOBAL LAYOUT AND LOCAL MICROSTRUCTURE TOPOLOGY OPTIMIZATION APPROACH FOR SPINAL CAGE DESIGN AND FABRICATION

GOVERNMENT SUPPORT

This invention was made with government support under grant numbers DE13416 and DE13608 awarded by the National Institutes of Health. The government has certain rights in the invention.

FIELD OF THE INVENTION

The present invention relates to a method of designing microstructure topology and more particularly, to a method of designing optimized microstructure topology for spinal cage design and fabrication.

BACKGROUND OF THE INVENTION

Conventional designs of spinal interbody fusion cages have mainly focused on providing immediate strength to maintain disc height and shielding bone grafts within the cage. As such, the geometric features of conventional designs show little distinction from each other and most designs fall into a category consisting of pipe shapes with thick shells as outer walls and a hollow interior space that brackets the fill of grafting materials.

For example, the following interbody fusion devices were tested in a study conducted by Kanayama: (A) the BAK device, a titanium threaded cage (D=13 mm, L=20 mm); (B) the BAK Proximity device, a titanium threaded cage (D=13 mm, L=20 mm); (C) the RAY TFC device, a titanium threaded cage (D=14 mm, L=21 mm); (D) the Danek TIBFD device, a stainless steel threaded cage (D=16 mm, L=26 mm); (E) the single oval Harms device, a titanium cylindrical mesh cage (17 mm×22 mm×13 mm); (F) the double oval Harms device, a titanium cylindrical mesh cage (D=14 mm, L=13 mm); (G) the Brantigan PLIF device, a carbon fiber rectangular cage (13 mm×13 mm×24 mm); (H) the Brantigan ALIF device, a carbon cylindrical rectangular cage (24 mm×35 mm×13 mm); (I) a femoral ring allograft device, a sliced femoral shaft (20 mm×24 mm×14 mm); (J) a bone dowel, a dowel-shaped allograft with one hole (D=14 mm, L=18 mm); and (K) the In Fix device, a titanium cylindrical implant (20 mm 29 mm×15 mm).

Conventional approaches can be further divided into subgroups defined by the threaded or non-threaded anchoring mechanism that the cage devices rely on to form rigid bonds with vertebral bodies. Threads may be provided along the entire outer surface of cylindrical cages, or may only be provided on two sides of wedge shaped cages.

Conventional hollow pipe designs guarantee sufficient reconstruction stiffness in arthrodesis and play a substantial role in stability for motion segments postoperatively. Nonetheless, the rigid shells may shield an implanted graft or ingrown bone tissue from sufficient mechanical stimulus, (known as "stress-shielding") thus increasing the risk for decreased mineralization and bone resorption and provide a stress-shielded environment inside the device. The concern for stress shielding has been widely discussed and investigated. The decreasing bone mineral density is believed to be attributable to the lack of mechanical stimuli which increases the risk of bone resorption.

In view of the foregoing, many modifications have been made to reduce the effect of stress shielding. A common approach was to adjust the pore size and the pore distribution on the shielding shell. It was concluded that the stress shielding effect was correlated with the largest pore size rather than the total porous area. However, it is important to note that increasing the largest pore size sacrifices the stiffness of the cage. This may yield excess compliance causing unexpected deformation and instability.

In general, the requirement for a shell thickness sufficient to be capable of carrying spinal loads leads to stress shielding. Conventional designs do not have the flexibility to meet the multiple design requirements necessary to achieve sufficient rigidity, reduced stress shielding, and large porosity for biofactor delivery.

Another approach which increases flexibility is by changing the base material to carbon fiber or a cortical bone allograft shaft. However, the material substitutes bring up additional issues of biocompatibility and immune response. In addition, there may be a limited supply of cortical bone allograft.

SUMMARY OF THE INVENTION

In view of the drawbacks of the conventional approaches, a new design approach for providing a lumbar spine interbody fusion cage is disclosed. The new design approach uses topology optimization algorithms to define the structural layout and the inner microstructures of the cage. This approach addresses the conflicting design issues of providing sufficient stability while at the same time providing appropriate porosity to deliver biofactors like cells, genes, and proteins and impart sufficient mechanical strain to maintain developing tissue. The interior architecture provided by the designed microstructures also reserves channel spaces for substance delivery in potential cell-based therapies and drug delivery. The present design approach allows a design to be modified for different patient types and allows the use of solid freeform fabrication techniques to manufacture the as-designed cage from commonly used biomaterials including but not limited to titanium, hydroxyapatite, tricalcium phosphate, polylactic acid, polyglycolic acid, and Poly (propylene fumarate).

As will be discussed in greater detail below, the present design approach has been used to generate a new prototype lumbar spine interbody fusion cage with a designed periodic microstructure that attains desired stability (displacements <0.9 mm), while maintaining compliance to avoid stress shielding and a large porosity for biofactor delivery.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

In accordance with the teachings of the present invention, a method of designing an interbody fusion cage is provided. The cage is designed to provide mechanical support, and scaffolding for tissue ingrowth and biofactor delivery to facilitate arthrodesis (spine fusion). The new design approach balances the conflicting requirements of providing stability for support, compliance to avoid stress shielding, and porosity for biofactor delivery.

As one skilled in the art may appreciate, stability requires a dense material while compliance and biofactor delivery require great porosity. The present invention employs an optimization approach to achieve a balanced design. Specifically, a material layout is created such that stability, compliance and porosity requirements are optimally balanced. Even more particularly, a unique two scale topology optimization approach is utilized to create the optimal material layout for desired stability, compliance and porosity.

The two scale topology approach includes a macroscopic or first scale topology optimization solution which provides the general density and location of material between, for example, the spinal vertebra, to limit displacement under an applied load for desired stability. The microscopic or second scale topology optimization solution provides the specific microstructure design that achieves the desired compliance while matching the predicted volume fraction of the macroscopic or first scale topology optimization solution.

Turning now to the drawing figures, a more detailed explanation of the present invention will be provided. First, referring to FIG. 1, a flowchart of the general methodology of the present invention is shown. The method begins in block 10 where the mechanical environment of a lumbar spine segment is modeled. While a lumbar spine segment is described herein, one skilled in the art will appreciate that the scope of the present invention is not limited thereto and other applications are readily available.

Figure 1:
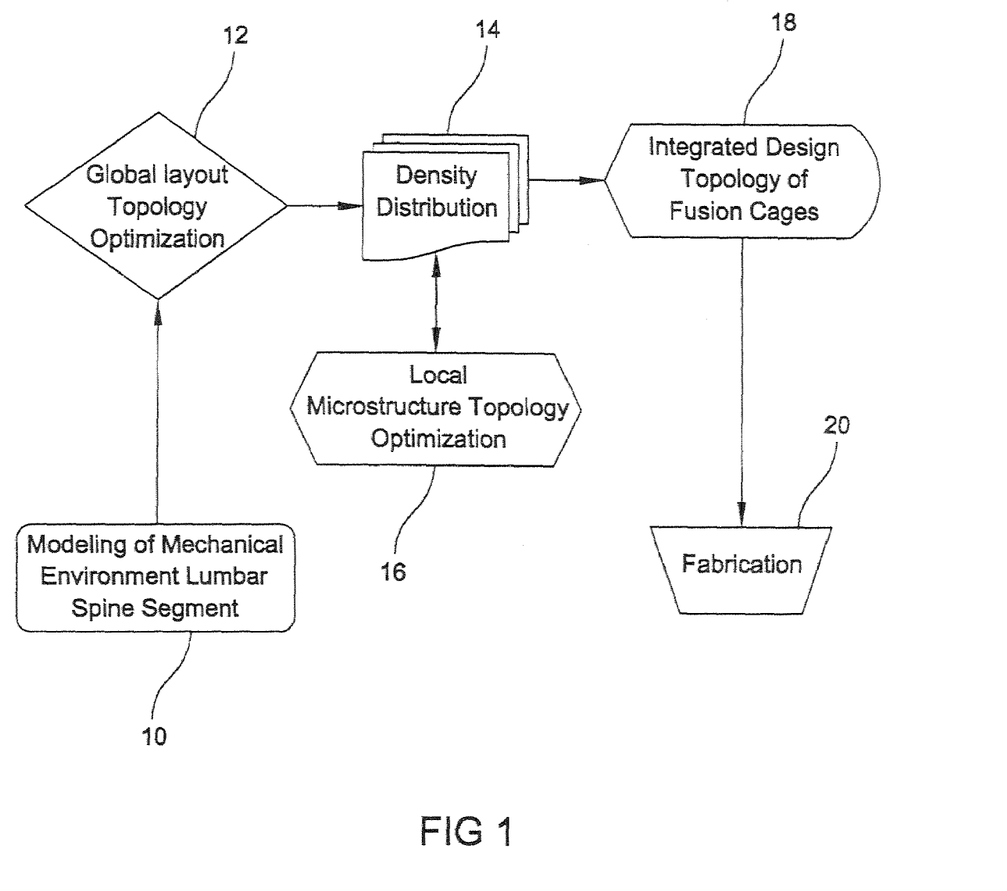
FIG. 1 is a schematic flowchart of the design process of the present invention.

In block 12, the method performs a global (i.e., macroscopic) layout topology optimization process. Then, in block 14, the method performs density distribution on the global layout topology optimization solution form block 12. The density distribution contemplates a local microstructure topology optimization solution from block 16. After completion of the density distribution process in block 14, the method proceeds to block 18. In block 18, the method provides an integrated (in terms of macro and microscopic solutions) design topology solution for the fusion cage. At block 20, the as-designed cage is fabricated.

In a preferred embodiment of the present invention, the process at blocks 10-14 employs a global topology optimization algorithm (e.g., Optistruct, Altair Computing, Inc.) to predict the global layout density under the constraint that displacements at the vertebral surface are less than 0.9 mm (strain <8%). To accomplish this, a finite element model is created to simulate the mechanical environment of the design domain within the disc space (block 10).

Figure 2:
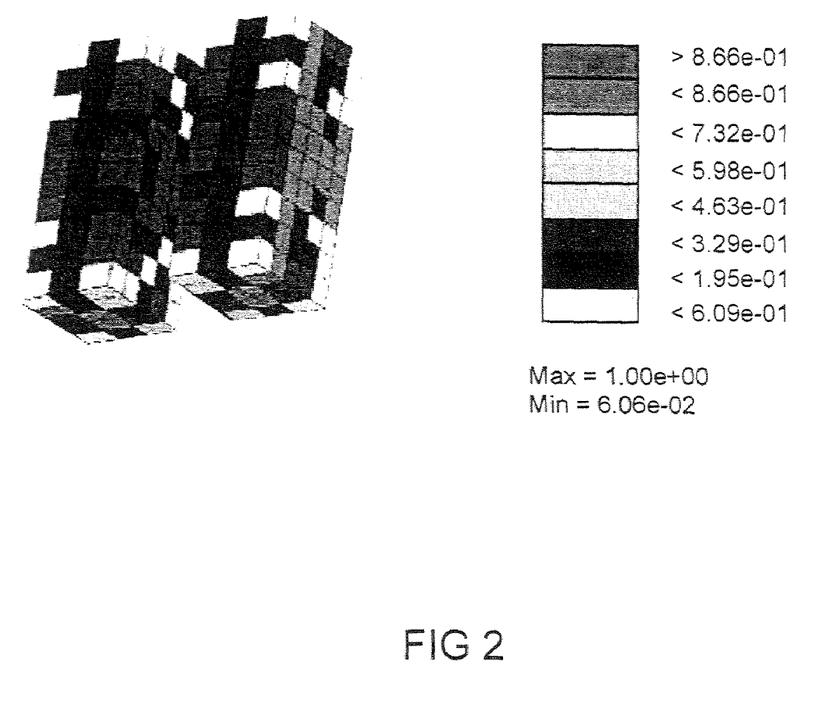
FIG. 2 illustrates a block configuration showing the corresponding density level of each element in a global optimal topology feature of the present invention.

As shown in FIG. 2, two rectangular blocks are established as the designable components to represent the location of the implanted cages and the multi-directional loads of the physiological range including compression, lateral bending, torsion, and flexion-extension are applied to the constructed segments (block 12). The optimal design of the cage topology is interpreted by cubic configurations of sub-elements corresponding to the respective material density between 0 to 1 where 0 indicates void space, 1 indicates solid segments, and values between 0 and 1 indicate material volume fractions (block 14).

Microstructures as Periodic Unit Cells in Material Constitution

Introduction of Microstructure Design

The global structural layout in blocks 10-14 creates transitional densities other than 0 or 1. This numerical difficulty could imply that the current mesh resolution cannot carry out the structure to achieve the objective function (stiffness or porosity), and is addressed as a mesh dependent problem. Different numerical techniques such as penalty schemes have been used in the past to force the element density to 1 or 0 under artificial material laws, which represent the element as a solid (base material) or a void (no material). Instead, according to the present invention, intermediate density values are used from the global topology optimization solution as representing microstructures defined at different length scales than the scale of the global optimization solution.

Figure 3:
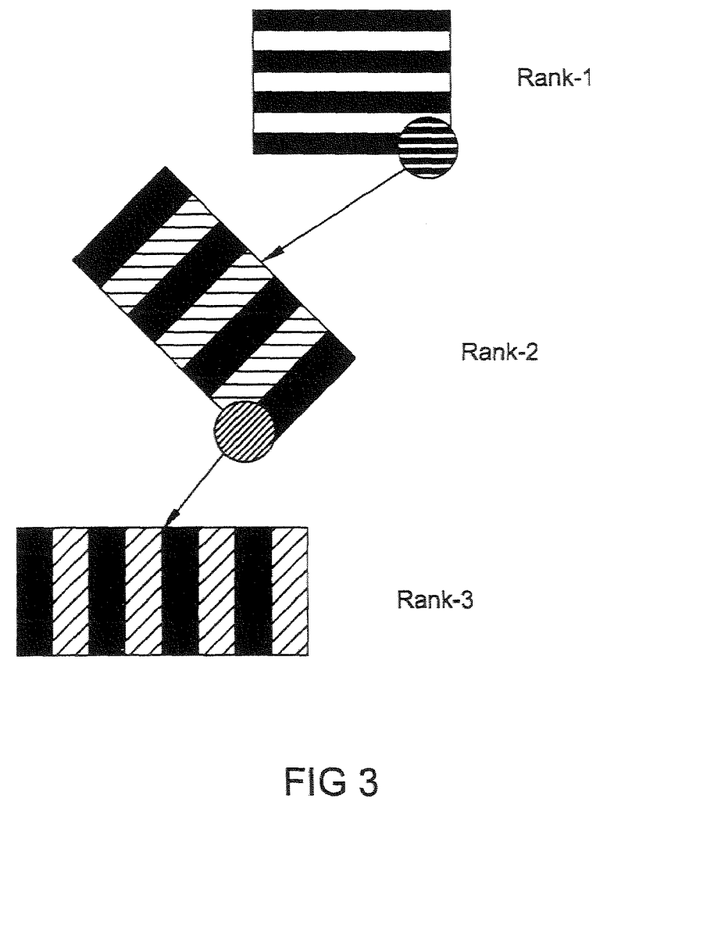
FIG. 3 illustrates how the microstructure of a composite material can be categorized into different ranks, each defined by different length scales, and the microstructure of a particular rank can be homogenized for its upper rank.

As shown in FIG. 3, the microstructure of the composite material used for the cage can be categorized into different ranks defined by different length scales, and the microstructure of a particular rank can be homogenized for its upper rank. This physical phenomenon allows a new approach to deal with an element having an intermediate density by introducing an additional rank of material design for the particular element.

Figure 4:
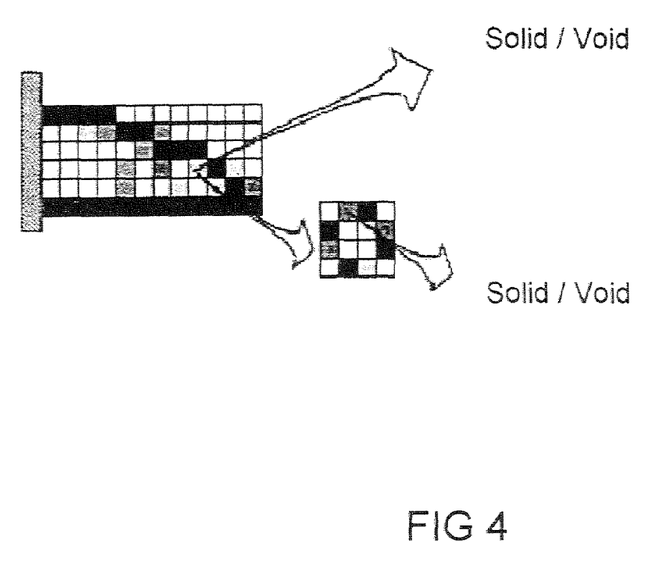
FIG. 4 illustrates how to obtain microstructures from a base material that can represent ambiguous elements having intermediate densities with physical verification.

As shown in FIG. 4, instead of choosing a cubic element of the global design (see FIG. 2) between 0 and 1, microstructures can now be obtained from a base material representing ambiguous elements of intermediate densities with physical verification. In other words, densities between 0 and 1 are replaced with a different microstructure scale. This microstructure is designed using microstructure or local topology optimization techniques (e.g., blocks 14 and 16 of FIG. 1).

It should also be noted that designing material microstructures allows for the creation of structures with an extremely wide range of elastic properties. For example, materials with negative Poisson's ratio (NPR), which expand transversely when subjected to an applied tensile load, can be used in many applications such as fasteners and shock absorbers. Furthermore, in the sense of design, the material may be designed with prescribed and specified values of material properties, such as elasticity, permeability, and dynamic performance, for a specialized application within the physical domain.

For the implementation of a material microstructure design for elasticity, a homogenization theory with periodic boundary conditions (PBC) can be used for the design domain.

Moreover, to theoretically calculate the effective properties of a material with a periodic microstructure pattern, a finite-element based homogenization technique can be utilized (e.g., S. Hollister, J. Brennan, and N. Kikuchi, A Homogenization Sampling Procedure for Calculating Trabecular Bone Effective Stiffness and Tissue Level Stress, J. of Biomechanics, 1994. 27(4): p. 433). The weak form of the equilibrium constitutive equation may be solved numerically using an Element-By-Element Preconditioning Conjugate Gradient (EBE-PCG) to obtain the effective elastic properties.

In accordance with the teachings of the present invention, two optimization algorithms, denoted as full topology optimization and restricted topology optimization, may be used to perform the microstructure scale design as described in the following sections.

Full Topology Optimization: Microstructure Design De Novo to Achieve Elastic Properties.

The design of a material microstructure using topology optimization was first implemented by O. Sigmund in 1997, and the problem can be considered as an optimal material distribution problem within the periodic design domain and solved using a Sequential Linear Programming (SLP) optimization technique. A generalized optimization problem formulation can be stated as (1):

$$\min_x w_1 \|C_1^H - C_1^*\|_{L_2} + w_2 \|C_2^H - C_2^*\|_{L_2} + \ldots s.t. \ C_3^H \geq C_3^* \quad (1)$$

Volume fraction constraints on the constituent base material

Symmetric of design domain constraints

Connectivity of structure constraints

Bounds on design variables

C can be any material property to be designed by minimizing the L2 norm of the difference between effective properties and target properties. wi are weighting parameters. This nonlinear optimization problem is solved using a Method of Moving Asymptotes (MMA), which was developed Svanberg in 1987. The current approach in literature, however, suffers from numerical difficulties when implemented in a three dimensional case.

The present invention provides two significant algorithmic enhancements to address the numerical difficulties associated with full topology microstructure design. The first algorithmic enhancement deals with the design dependency of initial guess, and convergence improvement. The second algorithmic enhancement deals with the application of image processing techniques during the topology optimization process to eliminate a checkerboard density pattern.

Turning to initial guess, because of the periodic boundary condition, the optimal result is not necessarily unique and depends significantly on the initial guess used in the design process. To address this issue, the present invention employs a low resolution mesh with a homogeneous density as a first initial guess in the optimization process. The optimization problem is then solved, and the resulting solution is meshed at a much finer resolution. The finer resolution solution is then used as a subsequent initial guess for the next set of iterations. This process is repeated and only ends when the best resolution is reached and converged. The detail design procedure is illustrated in the flow chart shown in FIG. 5.

Figure 5:
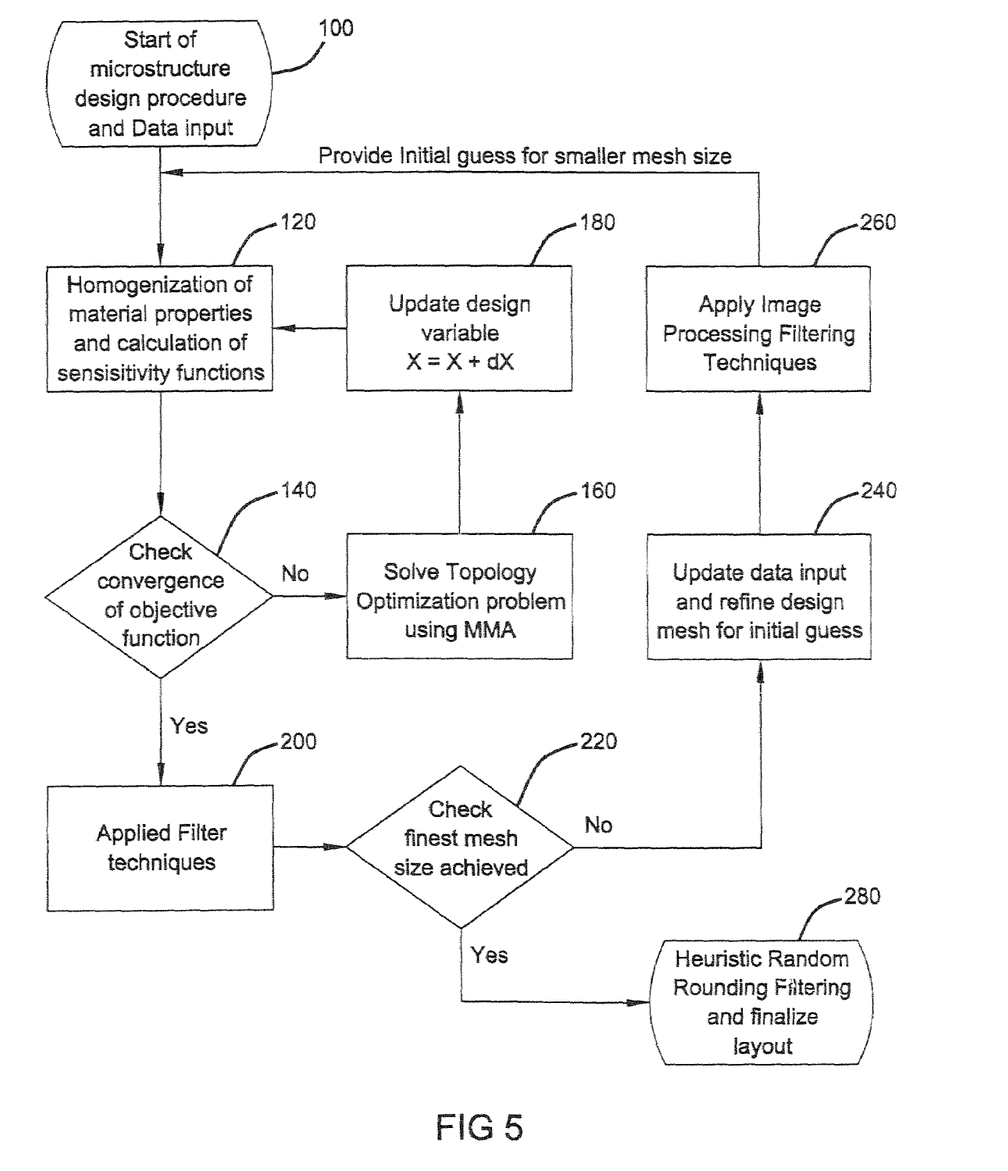
FIG. 5 is a flow chart of the detail design procedure.

As shown in FIG. 5, the method starts in block 100 where data such as material constraints and the low resolution mesh are input. The method proceeds to block 120 where homogenization of material properties and calculation of sensitivity functions are performed. Thereafter, the method proceeds to decision block 140.

In decision block 140, the methodology determines whether there has been a convergence of the objective function (stiffness or porosity). If not, the method proceeds to block 160. In block 160, the method solves the topology optimization problem using MMA as described above. Thereafter, the method proceeds to block 180. In block 180, the method updates the design variable based on the solved topology optimization problem from block 160. Next, the method returns to block 120. This loop is repeated until convergence of the objective function is determined to be achieved at decision block 140.

Once convergence is determined at decision block 140, the method proceeds to block 200. In block 200, the method applies filtering techniques to the design from decision block 140. Thereafter, the method proceeds to decision block 220. In decision block 220, the method determines whether the finest mesh size has been achieved within the design.

If not, the method proceeds to block 240. In block 240, the method updates the data input and refines the design mesh for the initial guess. Thereafter, the method proceeds to block 260. In block 260, the method applies image processing filtering techniques to the design (described in detail below). Next, the method provides the image processing filtered initial guess for a smaller mesh size from block 260 to block 120. This loop is repeated until the finest mesh size is achieved for the design at decision block 220.

Once the finest mesh is achieved at decision block 220, the method proceeds to block 280. In block 280, the method performs Heuristic Random Rounding Filtering and finalizes the design layout. The design layout is then used at blocks 14 and 16 in FIG. 1 to provide the integrated design of block 18.

As stated above, the second algorithmic enhancement of the present invention involves application of image processing techniques during the topology optimization process (block 260). This technique eliminates checkerboard density patterns from the design. To accomplish this, the element density is smoothed with surrounding elements using a Gaussian smoothing filter and also a connectivity filter within each optimization iteration. After elimination of checkerboarding, or rapid fluctuation in density over short scales, the final microstructure design still has a transitional density ranging between 0 and 1.

To minimize the impact of final filtering, a heuristic based random rounding technique is used in block 280. From the idea of integer programming, the density distribution in the design domain is considered as a probability distribution for discrete optimization. As such, infinite final designs generated from the probability table are available and the one that best satisfies all the design criteria is chosen to become the optimal microstructure layout.

Restricted Topology Optimization: Microstructure Design Assuming A Priori Topology to Achieve Elastic Properties Alternative Microstructure Options—Size Optimization (Restriction Design).

Figure 6:
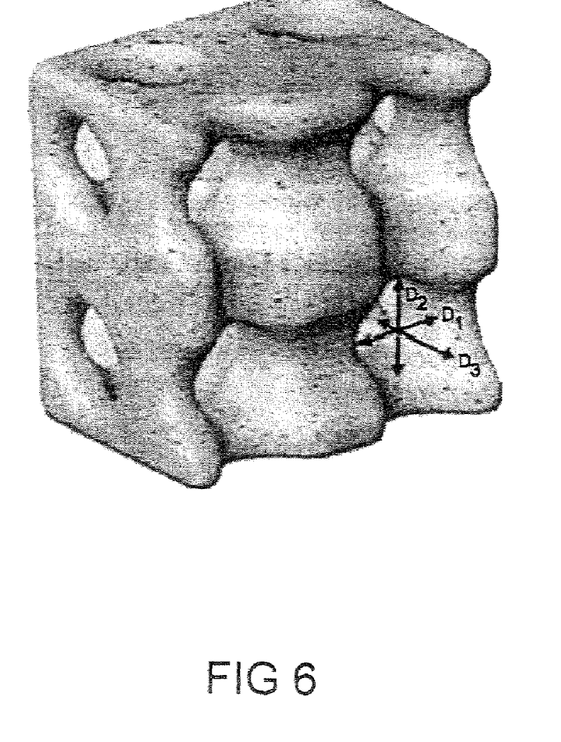
FIG. 6 is a cutaway showing the basic unit cell structure of interconnecting orthogonal cylinders having pores suitable for filling with regenerate tissue.

Another approach to define the microstructure of the periodic unit cell is to assume an initial topology with a restricted number of design variables describing the topology. For example, as shown in FIG. 6, one possible design is that of interconnecting cylindrical pores, where the design variables are the pore diameters.

In this approach, stiffness may be chosen to represent scaffold function and porosity to represent the scaffold's capability to enhance tissue regeneration. This can be further divided into two design options. As the first design option, if the primary goal is to design a scaffold such that the scaffold itself and regenerate tissue match desired mechanical properties while maintaining a base level of porosity, the optimal design problem, denoted as the stiffness design, can be written as:

Objective function:

$$\min_{E^{scaffold}, d_1, d_2, d_3} \left\{ \sum_{i=1}^{n} \left( \frac{C_i^{bone\ eff} - C_i^{tissue\ eff}}{C_i^{bone\ eff}} \right)^2 + \sum_{i=1}^{n} \left( \frac{C_i^{bone\ eff} - C_i^{scaffold\ eff}}{C_i^{bone\ eff}} \right)^2 \right\},$$

where n=1-9.

Constraints:

$$d_1, d_2, d_3 \leq 900\ \mu m$$

$$d_1, d_2, d_3 \geq 300\ \mu m$$

$$\frac{Vpore}{Vtotal} \geq \%\ \text{Porosity},$$

$$E^{scaffold} \geq E\min,$$

$$E^{scaffold} \leq E\max,$$

where design variables include $E^{scaffold}$ as the scaffold base material Young's modulus, and $d_1, d_2$, and $d_3$ as the three cylinder diameters. $C^{bone\ eff}$ is the effective stiffness of the target bone, $C^{tissue\ eff}$ is the regenerate tissue effective stiffness, and $C^{scaffold\ eff}$ is the scaffold effective stiffness. Thus the approach generates the structural interpretation consisting of three cylindrical chambers with computed diameters and the design modulus of corresponding configuration.

As the second design option, if the purpose of the design is to preserve large porosity for vascularization, plus both scaffold and regenerate tissue stiffness are maintained within an acceptable range, then the optimization problem denoted as the porosity design can be written as:

Objective function:

$$\max_{E^{scaffold}, d_1, d_2, d_3} \frac{Vpore}{Vtotal},$$

Figure 7:
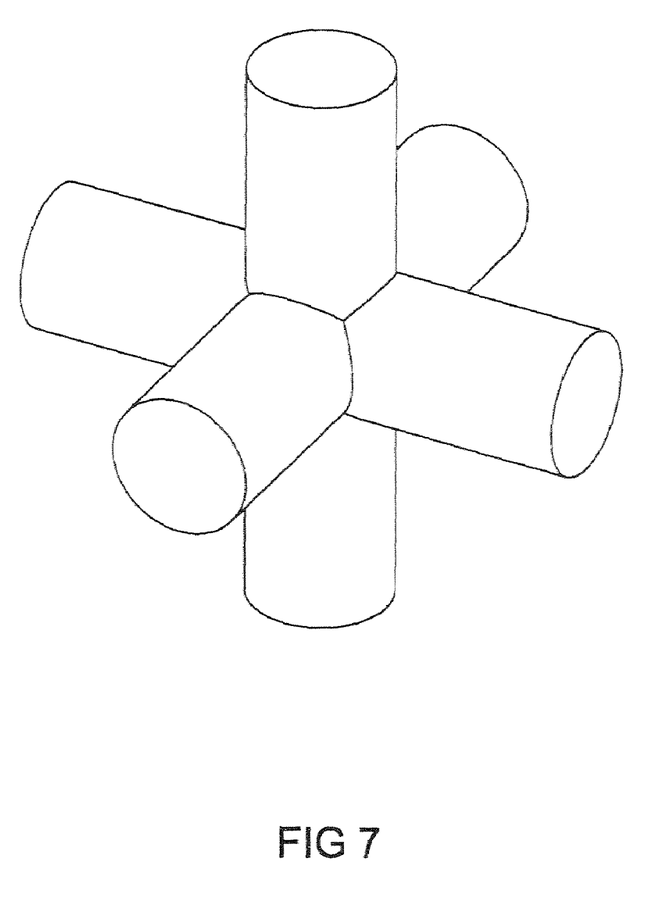
FIG. 7 illustrates the topology of a plurality of interconnecting cylinders for constructing internal pore spaces.

Constraints:

$$x_1 C_i^{bone\ eff} \leq C_i^{tissue\ eff} \leq x_2$$

where i=1-9; $x_2 > x_1$, $$\beta_1 C_i^{bone\ eff} \leq C_i^{scaffold\ eff} \leq \beta_2 C_i^{bone\ eff}$$

where i=1-9; $\beta_2 > \beta_1$, $$d_1, d_2, d_3 \leq 900\ \mu m,$$

$$d_1, d_2, d_3 \geq 300\ \mu m,$$

$$E^{scaffold} \geq E\min,$$

$$E^{scaffold} \leq E\max,$$

where $\alpha_1, \alpha_2, \beta_1$, and $\beta_2$ are scaling factors used to bound the scaffold and regenerate tissue effective stiffness and the variables are defined as above. Again, as shown in FIG. 7, the computed design variable defines the final topology of the interconnecting channels by three cylindrical chambers with three diameters in the periodic unit cell.

Defined Architecture to Elucidate the Complexity of the Topology in Ambiguous Density Interpretation of Block Conformations.

With the ability to design a material microstructure for specified properties, the transitional density range from the global topology optimization result can be dealt with. For a special spinal cage design case, the elasticity property of materials is considered. Refer to Z. Hashin and S. Shtrikman, A Variational Approach to the Theory of the Elastic Behaviour of Multiphase Materials, J. Mech. Phys. Solids, 1963. 11: p. 127.

Figure 8:
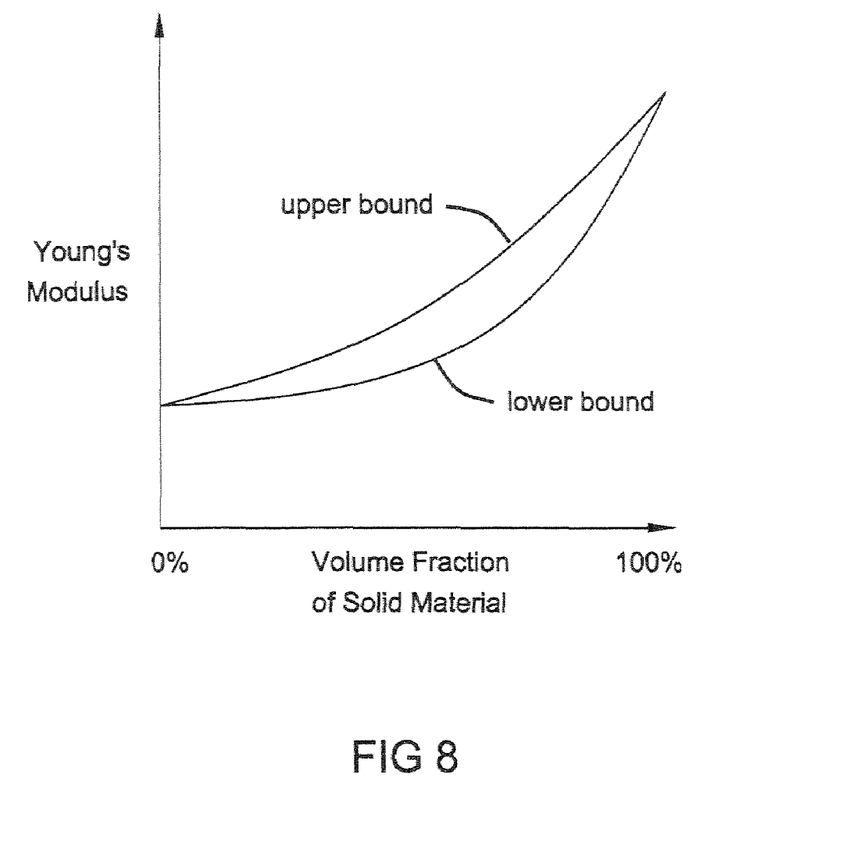
FIG. 8 is a graph showing that, for a particular elasticity property, there is an upper bound and lower bound of composite volume fraction to achieve.

The upper bound and lower bound of the elasticity of composite material are obtained theoretically. As shown in FIG. 8, for a particular volume fraction (or porosity), there is an upper bound and lower bound of stiffness a particular composite can achieve, or for a particular elasticity property, there is an upper bound and lower bound of composite volume fraction that is achievable. This provides two alternative ways to interpret the global topology density prediction.

For instance, assume a global element with a 0.5 density value. First, the element can be interpreted to have a unique microstructure with a 50% volume fraction and the objective material properties for microstructure design could be the upper or lower Hashin-Shtrikman bound depending on whether the global structure design should have extreme stiffness or compliance properties for that particular element. Second, an alternative interpretation is to consider that the element has specified anisotropic effective properties, and the microstructure is designed to achieve these particular properties with the smallest or largest volume fraction.

Defined Interconnected Channels with Carriers for Biofactor Delivery.

The microstructure design process of the present invention generates an interconnecting network of channels that define the biofactor delivery domain. The biofactors could include, for example, cells, genes, proteins or any combination thereof. The carriers could include hydrogels or polymers cast into the channels to release viable progenitor cells, genes or growth factors to achieve local bone tissue formation. Interconnecting channels can also provide favorable environments for vascularization as they provide conduits for angiogenesis and mass transportation to maintain the functions of new-forming tissues. Channels confined by surrounding microstructures also imply that the ingrown bone can receive direct mechanical stimulation transferred by the struts of the microstructures, thereby reducing stress shielding.

Integration of Global Layout and Local Microstructure Optimal Topology.

Referring again to FIG. 1, the integrated global and microstructure topology optimization approach of the present invention may be used to design, for example, a spinal cage, that meets the design requirements of immediate stability following implantation, sufficient compliance to avoid stress shielding, and high porosity for biofactor delivery. The global topology optimization algorithm described above is used to generate a global density distribution under physiologic loading (block 12). Immediate stability is addressed by constraining the total displacement at the vertebral surface to be less than a desired target. Total porosity for biofactor delivery and sufficient compliance is input as a constraint for global optimization. The result is a global volume fraction distribution ensuring sufficient porosity for biofactor delivery and avoidance of stress shielding.

In block 14, the layout density threshold is processed to segment the entire interconnected architecture into three separate material phases of a low porosity solid (45%~55%), a high porosity solid (20%~35%), and a completely voided region (0% material). A further discussion of this technique is provided with respect to FIG. 9 below. Note that the global material layout only provides porosity and does not define the topology of the porous microstructure. To define the porous microstructure in block 16, a local microstructure topology optimization method (FIG. 5) is used to generate periodic microstructures for the high percentage and low percentage solid regions that achieve Hashin-Shtrikman stiffness bounds for porous isotropic materials. The entire cage design can then be generated by repeating the periodic microstructures within the global density layout at blocks 14 and 16.

The density of the global layout from block 12 serves as a flag to assign the microstructure topology to different areas of the design. The overall cage volume fraction is closely held at the volume fraction of the original global layout optimal topology after the replacement of original global (cubic) elements with designed microstructures. The resulting porous cage architecture can therefore also serve the dual purpose of a delivery vehicle appropriate for therapeutic cell transplantation.

The fabrication of the designed cage in block 20 is achieved by automatically converting the image-design data from block 18 to a surface representation in .STL format. The image-design data is also converted to contour format. (It should be noted that rapid prototyping by stereolithography (SLA) has been used to fabricate a 5-fold magnified model layer in the cage middle region to investigate the internal connection of the microstructures.) The .STL and contour files provide the flexibility for adopting a variety of systems suitable for three-dimensional fabrication, including 3-D printing for the preparation of wax molds for later ceramic or polymer casting, photosensitive polymer synthesis in stereolithography (SLA) and direct metal deposition (DMD) for titanium manufacturing. Thus, the design methodology and spinal cage design also incorporate the capability for fabrication from current biocompatible and biodegradable materials into the integrated cage design.

Simulations

A prototype cage was produced to demonstrate the global feature design. The cage design domain was constructed with 8 by 4 by 4 elements, the size of which is exactly the same as the microstructure dimension. The volume fraction of the global optimal structure was 50%, with the density distribution represented in a block configuration similar to that shown in FIG. 2.

Figure 9:
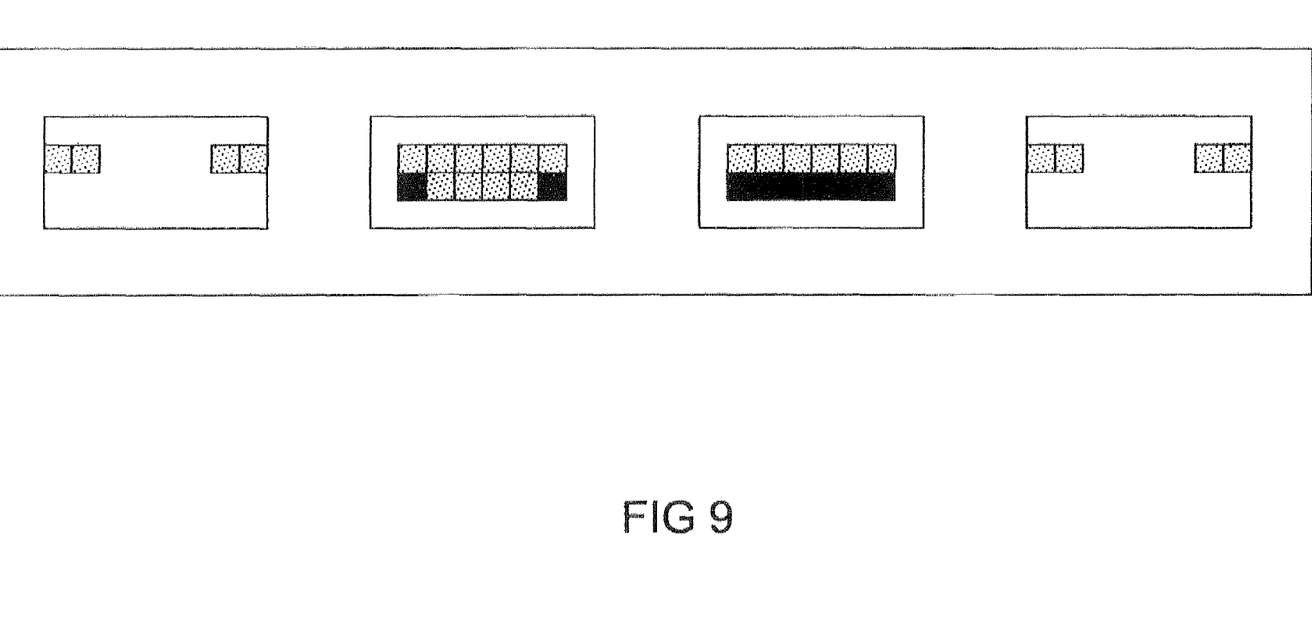
FIG. 9 is a plan view of each of the four layers of a global layout density, each layer segmented into three density phases after threshold processing.

FIG. 9 shows a plan view of each of the four layers in the employed block configuration. The layout density threshold was processed to segment the entire interconnected architecture into three separate material phases of 55% solid, 35% solid, and completely voided (0% material) so that the layout of each of the four layers is composed of one or more of the three values of grayscale corresponding to the regions of the material phases.

The local microstructure topology optimization method then generated periodic microstructures for the 55% and 35% solid regions in each of the four layers. In FIG. 9, the white regions will be replaced with a microstructure having a 55% volume fraction, the gray region will be replaced with a microstructure having a 35% volume fraction, and the black areas will be replaced with voids.

The prototype of the designed cage was achieved by automatically converting the image-design data to a surface representation in .STL format. The image-design data was also converted to contour .SLF format. The .STL format and contour .SLF format were then loaded in a 3-D printing machine for the preparation of wax molds. Advantageously, 3-D printing provides a way for large scale productions of complicated structures while maintaining consistency throughout multiple copies in the same batch.

Final prototypes were made (10 mm×10 mm×20 mm) with four microstructures on the short edge and eight microstructures on the long edge. Splitting the cage revealed the result of the interior topology from the global layout and subsequent microstructure replacement. Magnified images of the inner architectures of the wax mold clearly showed two alternating microstructures. Further, each microstructure performed well in terms of connectivity to adjacent unit cells.

It should be noted that the above description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of designing an interbody fusion cage comprising:
    defining operational parameters for the cage;
    defining a macroscopic structural layout for the cage satisfying the operational parameters;
    dividing the macroscopic structural layout of the cage into a plurality of discreet sub-segments;
    defining a density distribution of the macroscopic structural layout by determining a density level for each sub-segment;
    defining a microscopic structural layout for the cage by assigning pre-selected microstructures to the sub-segments in accordance with the density level of each sub-segment; and
    outputting an integrated design topology solution for fabrication of the interbody fusion case in response to the macroscopic structural layout and the microscopic structural layout.

2. The method of claim 1 wherein the operational parameters further comprise stability, porosity, and compliance.

3. The method of claim 1 wherein the step of defining the macroscopic structural layout further comprises executing a topology optimization algorithm for the cage based on the operational parameters.

4. The method of claim 1 wherein the step of defining the microscopic structural layout further comprises executing a topology optimization algorithm for the cage based on the density distribution.

5. The method of claim 1 further comprising integrating the microscopic structural layout and the macroscopic structural layout to provide a designed cage.

6. The method of claim 1 further comprising manufacturing the designed cage with solid free-form fabrication techniques.

7. The method of claim 1 further comprises categorizing the sub-segments into different ranks based on the density level of each sub-segment, each rank being defined by a different length scale; and
    homogenizing the microstructure of a particular rank to an upper rank.

8. A method of designing an interbody fusion cage comprising:

modeling a mechanical environment in which the cage is to be used;

performing a macroscopic layout topology optimization process to define a global layout topology solution for the cage;

performing a density distribution process on the global layout topology solution to define a density distribution of the global layout topology;

performing a microscopic layout topology optimization process to define a microstructure topology solution according to the density distribution; and integrating and outputting the global layout and microscopic topology solutions for fabrication of the interbody fusion case.

9. The method of claim 8 wherein the step of modeling the mechanical environment further comprises creating a finite element model to simulate the mechanical environment.

10. The method of claim 8 wherein the step of performing a microscopic layout topology optimization process to define a microstructure topology solution according to the density distribution further comprises representing microstructures of sub-segments of the cage with intermediate density values from the global topology optimization solution, the microstructures being defined at different length scales than the scale of the global optimization solution.

11. The method of claim 8 wherein the step of performing a microscopic layout topology optimization process to define a microstructure topology solution according to the density distribution further comprises:

employing a low resolution mesh with a homogeneous density as a first initial guess in the optimization process;

solving an optimization problem for the low resolution mesh to yield a rough solution;

meshing the rough solution at a finer resolution to yield a finer resolution solution;

using the finer resolution solution as a subsequent initial guess in the optimization problem; and repeating the above steps until a finest resolution solution is provided.

12. The method of claim 8 wherein the step of performing a microscopic layout topology optimization process to define a microstructure topology solution according to the density distribution further comprises:

defining one of stiffness and porosity as an objective function of the cage and the other of stiffness and porosity as a design variable;

inputting material constraints for the cage based on the objective function;

inputting a low resolution mesh of the microstructure topology based on the objective function as an initial guess design;

homogenizing the material constraints and calculating sensitivity functions for the initial guess design;

determining if a convergence of the objective function is achieved by the initial guess design;

if convergence is not achieved:
 solving a topology optimization problem in the optimization process using a method of moving asymptotes;
 updating the design variable in the initial guess design; and
 repeating until convergence of the objective function is achieved;

once convergence is achieved, filtering the initial guess design;

determining whether a finest mesh size has been achieved within the initial guess design;

if the finest mesh size is not achieved, updating the material constraints and refining the low resolution mesh to yield an updated initial guess;

applying image processing filtering techniques to the updated initial guess;

providing the image processing filtered initial guess for a smaller mesh size as a new initial guess design; and repeating the above steps until the finest mesh size is achieved.

13. The method of claim 12 further comprising performing heuristic random rounding filtering on the finest mesh size design to yield a final design layout.

14. The method of claim 12 wherein the image processing technique eliminates checkerboard density patterns.

15. The method of claim 14 wherein the image processing technique employs a Gaussian smoothing filter and a connectivity filter to smooth sub-segment densities within the cage relative to surrounding sub-segments.

16. The method of claim 12 wherein the stiffness objective function further comprises:

Objective function:

$$\min_{E^{scaffold}, d_1, d_2, d_3} \left\{ \sum_{i=1}^{n} \left( \frac{C_i^{bone\ eff} - C_i^{tissue\ eff}}{C_i^{bone\ eff}} \right)^2 + \sum_{i=1}^{n} \left( \frac{C_i^{bone\ eff} - C_i^{scaffold\ eff}}{C_i^{bone\ eff}} \right)^2 \right\},$$

Where n=1-9,

Constraints:

$d_1, d_2, d_3 \leq 900\ \mu m$ $d_1, d_2, d_3 \geq 300\ \mu m$ $\frac{Vpore}{Vtotal} \geq \%\ Porosity,$ $E^{scaffold} \geq Emin,$ $E^{scaffold} \leq Emax,$ wherein the material constraints include:

$E^{scaffold}$ as the scaffold base material Young's modulus;

$d_1, d_2,$ and $d_3$ as three cylindrical diameters of pores within the microstructure;

$C^{bone\ eff}$ as the effective stiffness of the target bone;

$C^{tissue\ eff}$ as the regenerate tissue effective stiffness; and $C^{scaffold\ eff}$ as the scaffold effective stiffness.

17. The method of claim 12 wherein the porosity objective function further comprises:

Objective function:

$$\max_{E^{scaffold}, d_1, d_2, d_3} \frac{Vpore}{Vtotal},$$

Constraints:

$x_1 C_i^{bone\ eff} \leq C_i^{tissue\ eff} \leq x_2 C_i^{bone\ eff}$ where i=1-9; $x_2 > x_1$, $$\beta_1 C_i^{bone\ eff} \leq C_i^{scaffold\ eff} \leq \beta_2 C_i^{bone\ eff}$$

where i=1-9; $\beta_2 > \beta_1$, $d_1, d_2, d_3 \leq 900\ \mu m$, $d_1, d_2, d_3 \geq 300\ \mu m$, $E^{scaffold} \geq Emin$, $E^{scaffold} \leq Emax$, wherein $\alpha_1, \alpha_2, \beta_1,$ and $\beta_2$ are scaling factors used to bound the cage and regenerate tissue effective stiffness and the material constraints include:

$E^{scaffold}$ as the scaffold base material Young's modulus;

$d_1, d_2,$ and $d_3$ as three cylindrical diameters of pores within the microstructure;

$C^{bone\ eff}$ as the effective stiffness of the target bone;

$C^{tissue\ eff}$ as the regenerate tissue effective stiffness; and $C^{scaffold\ eff}$ as the scaffold effective stiffness.

18. A method of designing an interbody fusion cage comprising:
  generating a global density distribution under physiologic loading for the cage using a global topology optimization algorithm including:
    a stability constraint that limits total displacement of the cage at a desired surface to be less than a target value; and
    a total porosity constraint that ensures desired biofactor delivering ability and compliance;
  segmenting the global density distribution architecture into a plurality of regions, each region having a material phase selected from:
    a low porosity solid phase;
    a high porosity solid phase; and
    a voided phase; and
  defining and outputting a porous microstructure for the cage by generating periodic microstructures for the regions having the high porosity solid phase and low porosity solid phase using a microstructure topology optimization method.

19. The method of claim 18 wherein:
  the low porosity solid phase regions are about 45%~55% solid;
  the high porosity solid phase regions are about 20%~35% solid; and
  the voided phase regions are about 0% solid.

20. The method of claim 18 wherein the step of defining a porous microstructure for the cage further comprises achieving Hashin-Shtrikman stiffness bounds for porous isotropic materials.

* * * * *

UNITED STATES PATENT AND TRADEMARK OFFICE
CERTIFICATE OF CORRECTION

| | |
|---|---|
| PATENT NO. | : 7,509,183 B2 |
| APPLICATION NO. | : 10/553851 |
| DATED | : March 24, 2009 |
| INVENTOR(S) | : Chia Ying Lin et al. |

It is certified that error appears in the above-identified patent and that said Letters Patent is hereby corrected as shown below:

Column 1, line 34            "L-20" should be --L=20--.

Signed and Sealed this

Fourteenth Day of July, 2009

JOHN DOLL
*Acting Director of the United States Patent and Trademark Office*